United States Patent
Mader (12)

(10) Patent No.: US 6,255,507 B1
(45) Date of Patent: Jul. 3, 2001

(54) PROCESS FOR PREPARING CYCLOPENTADIENYLIRON (II) ARENE COMPLEX

(75) Inventor: Roger A. Mader, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/156,225

(22) Filed: Sep. 18, 1998

(51) Int. Cl.[7] .............................. C07F 17/00; C07F 15/02
(52) U.S. Cl. ........................... 556/28; 556/1; 556/7; 556/13; 556/27; 556/30; 556/143
(58) Field of Search .................... 556/143, 1, 7, 556/13, 28, 27, 30

(56) References Cited

U.S. PATENT DOCUMENTS

| | | | |
|---|---|---|---|
| 4,851,430 | 7/1989 | Köpf-Maier et al. | 514/502 |
| 4,868,288 | 9/1989 | Meier | 534/15 |
| 4,992,572 | 2/1991 | Desobry et al. | 556/140 |
| 5,059,701 | 10/1991 | Keipert | 556/13 |
| 5,247,107 | 9/1993 | Desobry et al. | 556/52 |

FOREIGN PATENT DOCUMENTS

| | | |
|---|---|---|
| 3 404 443 A1 | 8/1985 | (DE) . |
| 0 314 618 A2 | 3/1989 | (EP) . |
| 0 314 618 B1 | 4/1994 | (EP) . |

OTHER PUBLICATIONS

Boeyens et al., "A Reinvestigation of the Ferrocene Oxidation by Iron (III) Chloride in 2–Butanone–Ethanol," South African Journal of Chemistry, vol. 37(1), pp. 32–34, (1984).

Sutherland, "η–Arene–η–Cyclopentadienyl Iron Cations and Related Systems," Journal of Organometallic Chemistry Library, vol. 3, pp. 311–342, (1977).

Tetrahedron, vol. 39, No. 24, pp. 4027–4095, (1983).

Dabirmanesh et al., "The Synthesis of Iron Sandwich Complexes by Microwave Dielectric Heating Using a Simple Solid $CO_2$–Cooled Apparatus in an Unmodified Commercial Microwave Oven," Journal of Organometallic Chemistry, vol. 460, pp. C28–C29, (1993).

Primary Examiner—Porfirio Nazario-Gonzalez

(57) ABSTRACT

Described are methods of preparing organometallic complexes, including cyclopentadienyliron (II) arene complexes.

23 Claims, No Drawings

PROCESS FOR PREPARING CYCLOPENTADIENYLIRON (II) ARENE COMPLEX

FIELD OF THE INVENTION

The invention relates to a process of preparing organometallic complexes, specifically cyclopentadienyliron (II) arene complexes.

BACKGROUND

Processes for preparing cyclopentadienyliron (II) arene complexes rely on the ligand exchange reaction of eta-5 dicyclopentadienyliron (II) (commonly referred to as ferrocene) with an arene, in the presence of a Lewis acid. This reaction can be represented as:

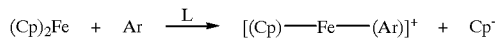

where Cp represents a cyclopentadienyl anion, Ar represents an arene or arene anion, and L represents a Lewis acid.

This reaction reportedly involves removal of one cyclopentadienyl anion from ferrocene by the Lewis acid as described and whose structures are given in the *Journal of Organometallic Chemistry Library* 1977, 3, 311, and *Tetrahedron* 1983, 39, 4037. It is theorized that the reaction produces a coordinately unsaturated cyclopentadienyliron (II) cation and a cyclopentadienyl anion-Lewis acid complex (anion-acid complex). The cyclopentadienyliron (II) cation coordinates with the arene to give the cyclopentadienyliron (II) arene complex product. The cyclopentadienyl anion-Lewis acid complex can undergo further chemistry, the nature of which depends on the particular Lewis acid used. A commonly used Lewis acid for these reactions is aluminum chloride ($AlCl_3$). Others include aluminum bromide, gallium chloride, zirconium tetrachloride, hafnium tetrachloride, boron trifluoride and tin tetrachloride. Mixtures of zirconium or hafnium tetrachloride with aluminum chloride and titanium tetrachloride have also been described (See EP-A 314,618 and U.S. Pat. No. 4,868,288).

In one prior art process of preparing cyclopentadienyliron (II) arene complexes, ferrocene is mixed with an arene, a Lewis acid, and a ferrous ($Fe^{+2}$) salt, to produce a cyclopentadienyliron (II) arene cation complex. (See U.S. Pat. No. 5,059,701). The reaction mechanism is said to be as follows: the Lewis acid removes one cyclopentadienyl ligand from a ferrocene molecule resulting in a cyclopentadienyl anion-Lewis acid complex (anion-acid complex) plus a cyclopentadienyliron (II) cation; the cyclopentadienyliron (II) cation complexes with an arene to form the product cyclopentadienyliron (II)arene cation complex; the cyclopentadienyl anion-Lewis acid complex transfers a cyclopentadienyl anion to another ferrous ion to produce another cyclopentadienyliron (II) cation which can undergo complexation with another arene molecule to produce an additional cyclopentadienyliron (II) arene cation complex.

U.S. Pat. No. 5,059,701 specifically and expressly teaches the use of divalent (ferrous) iron ($Fe^{++}$) ion as a reactant, as opposed to iron in any other oxidation state. The ferrous ion is said to react directly with the ferrocene. A described process of providing the ferrous ion is by reducing ferric ion to ferrous ion in a separate, preliminary processing step. The ferrous ion, produced beforehand in a separate step, is then added in the ferrous oxidation state to the other reactants (Lewis acid, ferrocene) to allow reaction of the ingredients toward the cyclopentadienyliron (II) arene complex.

It would be desirable, in the preparation of cyclopentadienyliron (II) arene complex compounds, instead of adding a source of ferrous ion to a reaction mixture, to add a source of ferric ion. This would allow, for one thing, the elimination of the separate, preliminary step described in the U.S. Pat. No. 5,059,701 patent of reducing the ferric ion to ferrous ion prior to reaction with the other reactants. It is described, however, in at least one previous teaching, that ferric ion (as compared to ferrous ion), when in the presence of ferrocene, reacts with the ferrocene to produce ferricenium tetrachloroferrate (III), $[Cp_2Fe]^+[FeCl_4]$. (See Boeyens et al., *The reinvestigation of the ferrocene oxidation by iron (III) chloride in 2-butanone-ethanol*, S. Afr. J. Chem. (1984) 37(1), 32–4). This teaching indicates that ferric ion added directly to reactants including ferrocene would result in production of ferricenium tetrachloroferrate (III), competing with the production of any other desired reaction product, such as a cyclopentadienyliron (II) arene cation complex.

SUMMARY OF THE INVENTION

The invention involves a process for preparing a class of organometallic complex salts, in particular, cyclopentadienyliron (II) arene cation complex salts. According to the invention, ferric ion can be added directly to reactants comprising ferrocene, a Lewis acid, and an arene, to prepare a cyclopentadienyliron (II) arene cation complex. The ferric ion can be converted to ferrous ion in situ, in the presence of ferrocene, with the ferrous ion subsequently reacting with a cyclopentadienylanion-Lewis acid complex to transfer a cyclopentadienyl anion to the ferrous ion and produce a cyclopentadienyliron (II) cation. The cyclopentadienyliron (II) cation can coordinate with an arene to produce a desired cyclopentadienyliron (II) arene complex. Competing reactions between ferrocene and the ferric ion do not lead to an unacceptable level of undesired ferricenium tetrachloroferrate (III) reaction product, and the combination of these reactants produces useful amounts of cyclopentadienyliron (II) arene cation complex.

Briefly, the invention provides a process for preparing cyclopentadienyliron (II) arene cation complexes by combining ferrocene, an arene, a ferric ion, and a Lewis acid. The process adds a source of ferric ion to the reaction solution instead of a source of ferrous ion, as described in earlier teachings; the ferric ion is reduced to a ferrous ion in situ, in the presence of the arene, ferrocene, and Lewis acid, thereby eliminating the separate, preliminary step described in the prior art of forming a ferrous ion from a ferric ion, and then adding the ferrous ion to the other reactants. The ferrous ion thereafter reacts as described in the prior art to produce a cyclopentadienyliron (II) arene cation complex.

A preferred embodiment of reaction sequence can be characterized as the combination of: 1) the in situ reduction of ferric ion to ferrous ion; and 2) a reaction of ferrocene, a ferrous ion, an arene, and a Lewis acid, to produce a desired cyclopentadienyliron (II) arene complex; e.g.,:

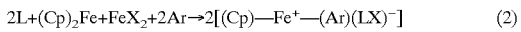

In equations 1 and 2 above, R represent a reducing agent, Ar represents an arene, X represents a halogen, and L represents a Lewis acid.

An aspect of the invention relates to a process for preparing a cyclopentadienyliron (II) arene cation complex. The process includes the step of providing a mixture comprising ferrocene, an arene, a Lewis acid, and a ferric ion. The cyclopentadienyliron (II) arene cation complex prepared by the invention can in the form of a salt with counterion A) be represented by the formula:

$$[(Cp)-Fe-(Ar)]^+_b A^{b-} \quad (3),$$

where Cp is an eta$^5$ complexed cyclopentadienyl anion ligand or an eta$^5$ complexed indenyl anion ligand, either of which may be substituted or unsubstituted; Ar is an eta$^6$ complexed arene anion ligand which may be either substituted or unsubstituted; and A is a b-valent anion where b can be 1, 2, or 3.

DETAILED DESCRIPTION

The reaction provides for the production of a cyclopentadienyliron (II) arene cation complex by reacting in a single vessel ingredients comprising ferrocene, an arene, a Lewis acid, and ferric ion; these ingredients will be referred to herein collectively but non-exclusively as "reactants," and when combined (either prior or subsequent to their reaction), as a "reaction mixture." Although the reactants can further include other useful ingredients such as an organic solvent, there is no need to directly add a source of ferrous ion.

For purposes of the present description, ferrocene refers to complexes having the general formula:

$$(Cp)-Fe-(Cp) \quad (4),$$

where each Cp independently represents a substituted or unsubstituted eta$^5$ complexed cyclopentadienyl anion or a substituted or unsubstituted indenyl anion. Substituents of the cyclopentadienyl anion or the indenyl anion may one or more, the same or different, monovalent radicals such as straight chain or branched chain alkyl or fluoroalkyl radicals, e.g., having from about 1 to about 10 carbon atoms, aryl, 1 to 10 carbon carboxylic acid ester, alkanoyl, benzoyl, chloro, or cyano. Examples of specific Cp anion ligands include the anions of methylcyclopentadiene, ethylcyclopentadiene, n-propylcyclopentadiene, n-butylcyclopentadiene, isobutylcyclopentadiene, 1,2-dimethylcyclopentadiene, 1,3-dimethylcyclopentadiene, trifluoromethylcyclopentadiene, phenylcyclopentadiene, cyclopentadienecarboxylic acid methyl and ethyl esters, acetylcyclopentadiene, benzoylcyclopentadiene, chlorocyclopentadiene, and cyanocyclopentadiene.

The arene reactant can be, for example, an aromatic compound having from about 6 to about 100 carbon atoms, or a heteroaromatic compound having from about 3 to about 100 carbon atoms and 1 to 10 heteroatoms, particularly a heteroaromatic compound containing non-peroxidic oxygen, nitrogen, or sulfur heteroatoms, either alone or in combination. The arene may be mononuclear, condensed polynuclear, or non-condensed polynuclear, and may be unsubstituted, monosubstituted, or polysubstituted, with identical or different monovalent radical substituents such as straight or branched chain alkyl, phenyl or other aryl, alkoxy, aryloxy, alkylthio, arylthio. Specific examples of suitable substituents include, for example: methyl, ethyl, propyl, isopropyl, n-butyl, sec-butyl, tert-butyl, isobutyl, n-pentyl, n-hexyl, 2-ehtylhexyl, n-octyl, methoxy, ethoxy, n-propoxy, isopropoxy, n-butoxy, phenoxy, n-propylthio, isopropylthio, and n-butylthio. The arene may comprise a single arene or a mixture of two or more arenes.

Examples of suitable arenes include benzene, toluene, o-xylene, m-xylene, p-xylene, mixed isomer xylene, mesitylene, durene, ethylbenzene, diethylbenzenes, propylbenzene, hexamethylbenzene, cumene, diisopropylbenzene, isobutylbenzene, anisole, ethoxybenzene, p-dimethoxybenzene, naphthalene, methylnaphththalenes, methoxynaphthalenes, 1,2-dihydronaphthalene, 1,2,3,4-tetrahydronaphthalene, biphenyl, diphenylmethane, triphenylmethane, diphenyl ether, stilbene, biphenylene, paracyclophane, anthracene, phenanthrene, 9,10-dihydroanthracene, fluorene, triphenylene, pyrene, perylene, chrysene, chromene, coronene, naphthacene, xanthene, thioxanthene, pyrrole, furan, benzofuran, dibenzofuran, benzopyran, carbazole, triophene, benzothiophene, indole, indene, acridine, and benzoxazine. Other examples of suitable arenes may be found by consulting any of many chemical handbooks.

Lewis acids are known in the art of organometallic compounds. See for example U.S. Pat. No. 5,059,701, the disclosure of which is incorporated herein by reference. In the process of the invention the Lewis acid can be any Lewis acid capable of forming a complex with a Cp anion, and that is sufficiently reactive to allow transfer of the Cp anion to a ferrous anion to accomplish the reaction described herein to produce a cyclopentadienyliron (II) arene cation. Examples of preferred Lewis acids include aluminum halides such as aluminum chloride and aluminum bromide, boron trifluoride, and gallium halides, sublimed aluminum chloride being the most preferred.

The Lewis acid may include a single Lewis acid or a mixture of two or more Lewis acids. In addition to the above-described first group of preferred Lewis acids, one or more of a second group of preferred Lewis acids can be included in the reaction mixture, as is known in the organometallic chemical art, e.g., to improve the yield of the organometallic complex reaction product. Examples of secondary Lewis acids include tetrachlorides of tin, titanium, zirconium and hafnium. These Lewis acids are relatively reactive and can be used as rate-enhancing additives. They are generally unsuitable for use as the only Lewis acid in the reaction mixture because of their relatively strong reactivity. Thus, the Lewis acids of this second preferred group can generally be used in combination with one or more other Lewis acid, such as a Lewis acid from the above-identified first preferred group.

Ferric ion ($Fe^{+3}$) can be provided from any source of ferric ion and in any form that will not introduce to the reaction mixture other chemical species that substantially interfere with the desired overall reaction to produce a cyclopentadienyliron (II) arene complex. The source of ferric ion should comprise a ferric ion that is sufficiently soluble in the reaction mixture, and sufficiently reactive, to provide an amount of ferric ion sufficient to undergo useful reduction to ferrous ion and reaction toward the desired cyclopentadienyliron (II) arene cation complex. An example of a useful source of ferric ion can be a ferric salt. For ferric ion introduced as a ferric salt it can be desirable that the anion component of the ferric salt not substantially interfere with the production of cyclopentadienyliron (II) arene cation complex. The ferric salt can preferably be in an anhydrous, or nearly anhydrous form, and can preferably not contain any functionality that is sufficiently acidic to significantly protonate the cyclopentadienyl anion.

A preferred source of ferric ion is a ferric salt such as a ferric halide, preferably ferric chloride. Examples of other useful sources of ferric ion can be carboxylate salts, sulfate salts, and nitrate salts, of ferric ion.

According to the invention, the ferric ion can be reduced to a ferrous ion in situ, in the reaction mixture, in the presence of the other reactants including ferrocene. The reduction of ferric ion to ferrous ion can take place by any method that does not substantially hinder the desired overall reaction toward a cyclopentadienyliron (II) arene cation complex, for example by method where a reducing agent causes reduction of the ferric ion to a ferrous ion, while at the same time not substantially hindering the desired overall reaction. Preferred reducing agents include unsaturated, generally aromatic compounds such as arenes.

In a preferred embodiment of the invention the ferric ion can be provided by dissolving a ferric halide in the reaction solution, ad the ferric ion can be reduced to ferrous ion by reacting the ferric ion with an arene, in an oxidative halogenation. The arene is halogenated and becomes a stable by-product of the reaction (ArX). Such an oxidative halogenation reaction can be illustrated in general as follows:

$$Ar + FeX_3 \rightarrow ArX + FeX_2 \quad (5),$$

wherein Ar represents an arene and X represents a halogen. Most preferably the arene that functions as the reducing agent can be the same arene that is added as a reactant to the reaction mixture to coordinate with the cyclopentadienyliron (II) cation to produce the desired cyclopentadienyliron (II) arene complex reaction product; thus, most preferably the arene reactant and the reducing agent can be the identical arene compound.

An especially preferred example of the oxidative halogenation of equation 5 is the reaction between meta xylene and ferric chloride to produce ferrous chloride and 2,4-di-methyl chlorobenzene:

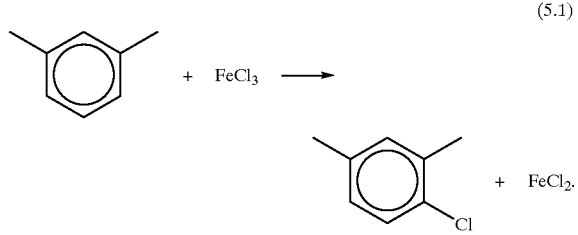

(5.1)

The amount of each reactant included in the reaction mixture can be any amount effective to produce a useful yield of cyclopentadienyliron (II) arene cation complex. Generally, it can be preferred to use amounts of each reactant that are stoichiometrically appropriate according to equations 1 and 2, above.

Preferably the reaction mixture contains at least 1 mole ferric ion per mole ferrocene; e.g., from about 0.8 to 1.2 mole ferric ion.

The reaction mixture can preferably include at least a stoichiometric amount of the reducing agent R, e.g., according to equation 1 above, at least about one mole reducing agent per mole ferrocene.

The reaction mixture can also preferably include at least a stoichiometric amount of arene, e.g., according to equation 2, at least 2 moles of arene based on one mole of ferrocene. If the same arene is used as both the reducing agent of equation 1 and the arene reactant of equation 2 (as illustrated, e.g., in equation 6 infra), a further mole of arene is required, making a total of 3 moles arene per mole ferrocene for the combined reactions. It can be useful or preferable to include up to a 5 to 10 fold molar excess of arene, the arene can also be used as the reaction solvent (described infra).

Preferably the reaction mixture contains at least about 1 mole of Lewis acid per mole ferrocene, more preferably between 1.5 and 3 moles, as either a single compound or as a mixture of two or more Lewis acid compounds. If a mixture of a Lewis acid from the first preferred group identified supra is used with a Lewis acid from the second preferred group, also identified supra, it can generally be preferred to use a small amount of the more reactive Lewis acids of the second group. A quantity of between 0 and 0.2 mole of the more reactive Lewis acid, per mole ferrocene, can be preferred, with an amount below about 0.1 mole being most preferred.

A reducing metal may optionally be included as a reactant in the reaction mixture as an antioxidant to prevent undesired oxidation of other reactants. The reducing metal can be any metal that will act to prevent such oxidation, and the metal can preferably be in a finely divided form to give a large surface area. Antioxidants generally, and reducing metals more specifically, are known in the chemical art and include such reducing metals as aluminum, magnesium, and zinc. A preferred reducing metal for use in the present invention is aluminum, most preferably in the form of aluminum powder. The reducing metal may be included as a reactant in any useful amount, as will be apparent to those skilled in the organometallic chemistry art, and can preferably be present in an amount in the range from about 0.1 to 1 mole reducing metal per mole ferrocene.

The reaction can preferably take place in an appropriate type and amount of solvent. Useful solvents can include organic compounds that are non-basic enough to avoid complexing with the Lewis acid reactant, and that do not compete with the arene for complexing with the iron ion. The solvent can be any appropriate organic compound, as is known in the chemical art for such a purpose, but if practical, the solvent used can preferably be the same arene compound that is used as a reactant as described above in either equation 1 (where the reducing agent R represents an arene), or equation 2, supra. In cases where it is not feasible to use the same reactant arene compound as a reaction solvent, for example in the case of relatively more expensive arenes, a different organic solvent may be used. Specific examples of useful solvents include non-polar, non-reactive, organic liquids, for example, alkanes, arenes, and cycloalkanes, either as pure compounds or as mixtures. Specific examples of useful solvents include cyclohexane, methylcyclohexane, decahydronaphthalene, heptane, octane, and similar straight chain and branched alkanes, as well as mixtures containing these or other organic solvents, such as a commercial octane fraction.

As little moisture as possible should be present in the reaction mixture. While it is preferred that the reaction be run under anhydrous conditions, such as in the inert atmosphere of dry nitrogen, this is not required, and it is also possible to run the reaction under a normal, ambient air atmosphere.

A preferred embodiment of the reaction can be characterized by the equations:

$$Ar + FeX_3 \rightarrow ArX + FeX_2 \quad (6a),$$

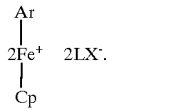

(6b)

wherein Ar, Cp, X, and L are as defined.

In a specific example of this preferred embodiment, the arene comprises meta xylene, the source of ferric ion comprises ferric chloride, and the Lewis acid comprises aluminum chloride:

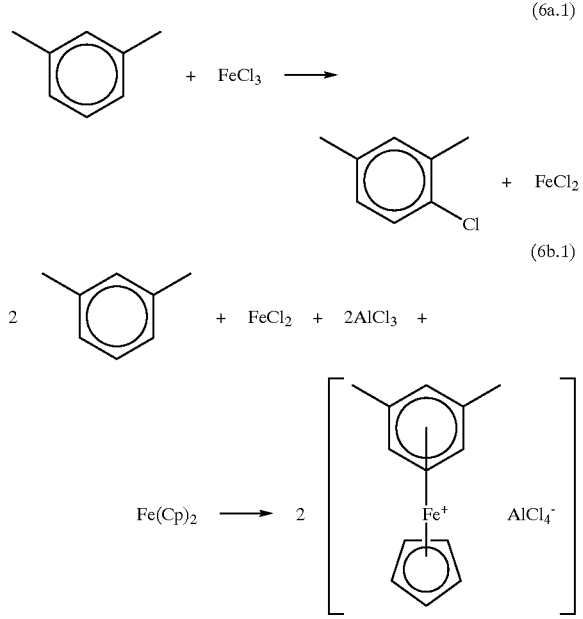

As will be apparent to a skilled artisan, other arenes, reducing agents, and Lewis acids can be substituted for those shown in equations 6a.1 and 6b.1 to provide analogous reaction schemes for the production of other similar cyclopentadienyliron (II) arene complexes.

According to the process, reactants comprising ferrocene, an arene, ferric ion, and a Lewis acid, can be provided together in a single reaction vessel to form a reaction mixture. The reaction vessel can be any suitable container, and preferably includes means for mixing the reaction mixture, means for adding or removing heat energy to and from the reaction mixture, means for monitoring the temperature of the reaction mixture, means for controlling the pressure over the reaction mixture, and means for providing an inert atmosphere over the reaction mixture.

The reactants may be provided to the reaction vessel in any order. Once the reactants are combined, the reaction can typically be promoted by heating the reaction mixture with an external heat source, for example a heating mantle. Although the reaction is typically exothermic, which can provide a certain amount of heat energy to the reaction, it is typically useful to add additional heat energy to the reaction mixture to further promote the desired reaction and to increase yield of the desired complex. In reactions that are very rapidly exothermic, it may be desirable or advantageous to combine the reactants slowly. For example, it may be desirable or advantageous to add the ferrocene slowly to the other reactants.

The reaction may be run at any conditions of temperature and pressure that are effective to result in the production of a cyclopentadienyliron(II) arene complex. For instance, useful reaction temperatures can be between 20 and 250 degrees Celsius (C.), with temperatures between 80 C. and 140 C. being preferred. The pressure can be standard atmospheric pressure, or elevated pressure may be used if desired, for example if one of the reactants is volatile.

The reaction can be allowed to proceed for any period of time sufficient to produce a useful yield of the desired cyclopentadienyliron (II) arene complex reaction product. For example the reaction can be allowed to proceed for a time between 0.1 and 24 hours. The end of the useful reaction can be determined by monitoring the yield percent of reaction product.

Upon completion of the reaction the reaction mixture can be cooled and quenched. This can be accomplished by Lewis acid hydration, meaning the reaction mixture is combined with either chilled water, a chilled mixture of alcohol and water, or a chilled absolute alcohol (e.g., methanol, ethanol, isopropanol, etc.) followed by water. External cooling can be simultaneously applied to the reaction vessel. The cooled and quenched reaction mixture can be added to a mixture of ice and water, e.g., in an amount, for example, of about 2 liters ice and water per mole of ferrocene. This will result in a two phase mixture, one phase being of ice and water and the other phase being organic. The organic phase will contain organic soluble materials, and the desired cyclopentadieneyliron (II) arene complex will be contained in the aqueous phase.

It is sometimes advantageous to add a mild reducing agent to the aqueous phase to reduce ferricenium ion that may have formed back to ferrocene. Generally, ascorbic acid can be a preferred such mild reducing agent. Sodium sulfite may also be used.

The reaction mixture, including the cyclopentadienyliron (II) arene complex, can be processed by techniques known in the organic chemistry art to isolate or purify the desired cyclopentadienyliron (II) arene complex product. The different phases of the reaction mixture, the aqueous phase (containing the desired product), and the organic phase, can be separated by known methods. The aqueous phase may be purified by extracting the impurities with a suitable organic solvent or solvent mixture. Preferred extraction solvents include non-polar, water-immiscible solvents that dissolve ferrocene and the arene. Examples of preferred solvents include cyclohexane, ethyl acetate, and dichloromethane. The cyclopentadienyliron(II) arene complex reaction product is generally present in the aqueous phase as a Lewis acid complex salt, for example a salt of $AlCl_4^-$, or the like.

The aqueous phase may be filtered to remove any residual reducing metal powder.

It can be desirable to exchange the Lewis Acid anion of the originally-formed complex for a substitute anion (designated $A^-$), to provide a complex with a different anion, and that might be useful for a specifically desired application. For example it may be desirable to prepare a reaction product complex including a non-nucleophilic anion that may be relatively more effective in combination with the complex to act as a photoinitiable polymerization catalyst. Nucleophilic anions such as chlorine can interfere with the action of a photocatalyst by complexing iron and preventing monomer complexation. Non-nucleophilic anions such as $PF_6^-$, $SbF_6^-$, $BF_4^-$ can be preferred for their relatively higher catalytic activity. Although the ion exchange may proceed as indicated hereinafter, the ion exchange may be done by any process known to be useful in the chemical art for ion exchange.

In general, the ion exchange reaction can be characterized by the following reaction:

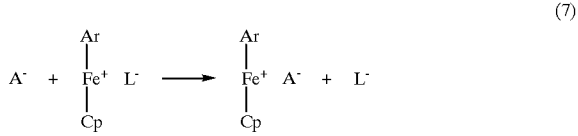

(7)

As a specific example of this reaction, a tetrachloro aluminate anion (AlCl$_4$) can be replaced with a hexafluoroantimonate anion as follows:

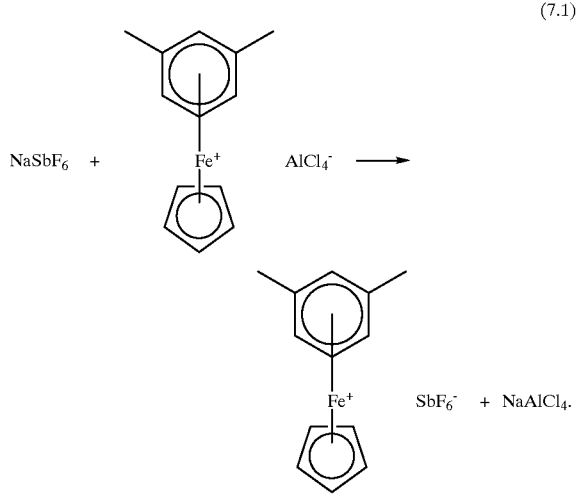

(7.1)

The desired anion-exchanged product can be precipitated from the aqueous phase by adding a water soluble salt or acid of the desired anion to produce a slurry of the complex in water. Examples of such a process include the precipitation of hexafluorophosphate salts (PF$_6^-$) by addition of an ammonium, sodium, or potassium hexafluorophosphate or hexafluorophosphoric acid, the precipitation of a hexafluoroantimonate salt (SbF$_6^-$) by addition of sodium hexafluoroantimonate, and the precipitation of a tetrafluoroborate salt by addition of tetrafluoroboric acid. The desired complex reaction product may be removed from the slurry by known methods, such as by filtration or by extraction with a suitable organic solvent, such as dichloromethane.

The process of the invention can be used to prepare cyclopentadienyliron (II) arene cation complex salts having the general formula:

[(Cp)—Fe—(Ar)]$^+_b$A$^{b-}$, where Cp is an eta$^5$ complexed cyclopentadienyl anion ligand or an eta$^5$ complexed indenyl anion ligand, either of which may be substituted or unsubstituted; Ar is an eta$^6$ complexed arene anion ligand which may be either substituted or unsubstituted; and A is a b-valent anion where b can be 1, 2, or 3. The counterion (A$^{b-}$) can be, as illustrative examples, a chlorinated, fluorinated, hydroxylated, alkylated, or arylated anion of P, As, Sb, Bi, B, Al, Ga, In, Sc, Ti, Zr, V, Cr, Mn, Fe, Co, Cu, Zn, Sn, and Ce. In the case of anions containing alkyl or aryl groups, the alkyl or aryl groups may be substituted or unsubstituted. Illustrative examples of other suitable anions include: (phenyl)$_4$B$^-$, (phenyl)$_3$(alkyl)B$^-$, (alkyl)$_4$B$^-$, where alkyl can be ethyl, propyl, butyl, isobutyl, hexyl, and the like, (phenyl)$_3$(benzyl)B$^-$, BF$_4^-$, PF$_6^-$, AsF$_6^-$, SbF$_6^-$, FeCl$_4^-$, SnCl$_5^-$, AlF$_4^-$, GaCl$_4^-$, TiCl$_4^-$, SbF$_5$OH$^-$, pentafluorophenyl borate, and tetra-(3,5-bis-trifluoromethylphenyl borate). Preferably the anion can be BF$_4^-$, PF$_6^-$, SbF$_6^-$, SbF$_5$OH$^-$, AsF$_6^-$, SbCl$_6^-$, or C(SO$_2$CF$_3$)$_3^-$. Additional suitable anions, A$^{b-}$, include the organic sulfonates. Illustrative of suitable sulfonate-containing anions include methanesulfonate, trifluoromethanesulfonate, benzenesulfonate, p-toluenesulfonate, p-chlorobenzenesulfonate, p-trifluoromethylbenzenesulfonate, and the like. Trifluoromethanesulfonate can be particularly preferred. Additional suitable anions include the anions of strong acids such as perchlorate, sulfate, and nitrate.

Organometallic complex cations prepared according to the process of the invention can be useful for applications including as light-activated thermal catalysts for a variety of polymerization reactions including polymerization of polyols and polyisocyanates to provide polyurethanes, epoxides to provide epoxy resins, cyantes to provide polytriazines, and vinyl ethers to provide polyvinyl ethers. See U.S. Pat. No. 5,059,701. Additionally, complex cations that can be prepared according to the process of the invention can be useful in two-stage polymerization (curing).

EXAMPLES

Preparation of cyclopentadienyliron (II) m-xylene hexafluoroantimonate

A 500 ml flask was purged with nitrogen and to it was added 28.8 grams of ferric chloride, 53.6 grams of aluminum chloride, 30.8 grams of ferrocene, and 150 grams of m-xylene. After the addition was complete an exothermic reaction ensued and the temperature rose to 60 degrees Celsius (60 C.). After the exotherm started to subside the reaction was heated to 100 C., and held at that temperature for one hour. Aluminum powder (1.3 grams) was then added, and the heating continued at 125 C. for 24 hours. The reaction mixture was cooled to 22 C. then quenched by slowly adding it to 360 ml of water which had been cooled to 10 C. The temperature of the quenched mixture was kept below 26 C. throughout the addition. The mixture was stirred at 22 C. for one hour after the addition was complete. The mixture separated into its aqueous and organic phases. The aqueous phase was separated from the organic layer, filtered, and washed two times with 70 ml of ethyl acetate and two times with 50 ml of heptane. The aqueous solution was stirred and to it was added 111 grams of sodium hexafluoroantimonate over a period of 30 minutes. The mixture was stirred an additional 15 minutes after which the product was filtered and washed with water 400 ml of water and 100 ml of isopropyl alcohol. After drying, 120 grams (80% of theoretical) of cyclopentadienyliron (II) m-xylene hexafluoroantimonate was obtained.

Preparation of cyclopentadienyliron (II) mesitylene hexafluoroantimonate

Using a procedure identical to the one described above except substituting 170 grams of mesitylene for m-xylene, there was obtained 96 grams(6 1% of theoretical) of cyclopentadienyliron (II) mesitylene hexafluoroantimonate.

The following example illustrates a procedure in which the reaction was quenched by sequentially adding ethanol and water to the reaction mixture.

Preparation of cyclopentadienyliron (II) o-xylene hexafluoroantimonate

A 500 ml flask was purged with nitrogen and to it was added 28.6 grams of ferric chloride, 44.7 grams of aluminum chloride, 30.8 grams of ferrocene, and 150 grams of o-xylene. The mixture was heated to 100 C. for three hours. After this time 1.0 gram of aluminum powder was added and the reaction mixture heated to 140 C. for 15 hours. The flask was cooled to 22 C. with ice water and 69 grams of ethanol, and 360 ml of water were added respectively while keeping the reaction temperature below 24 C. The aqueous phase was separated and washed with 50 ml of ethyl acetate. To this was added 62 grams of sodium hexafluoroantimonate and the mixture was stirred for 15 minutes. The product was filtered and dried to give 98 grams (64% of theoretical) of cyclopentadienyliron (II) o-xylene hexafluoroantimonate.

As will be appreciated by those skilled in the chemical art, other cyclopentadienyliron (II) arene complexes, being the same except having a different arene ligand or a different counterion, could be prepared by methods similar to those described immediately above, by substituting the reactants with other chemically appropriate reactants. For example, cyclopentadienyliron (II) arene complexes that are similar to these exemplified compleses could be prepared by substituting the arene reactant with, for example, mixed xylene, isopropyl benzene, toluene, another alkyl substituted benzene. The counterion A can be similarly substituted with another to prepare an analogous complex with the substitute counterion.

What is claimed is:

1. A process for preparing a cyclopentadienyliron (II) arene cation complex, the process comprising the step of providing a mixture of reactants comprising ferrocene, an arene, a Lewis acid, and a ferric ion, in amounts and under conditions sufficient to effect reaction of the reactants to a cyclopentadienyliron (II) arene cation complex.

2. The process of claim 1 wherein the ferric ion is reduced, in the presence of ferrocene to a ferrous ion.

3. The process of claim 2 wherein the ferric ion is provided by dissolving a ferric salt in the reaction mixture, and the ferric ion is reduced to a ferrous ion in the presence of ferrocene, the Lewis acid, and the arene.

4. The process of claim 2 wherein the arene acts as a reducing agent to reduce the ferric ion to a ferrous ion.

5. The process of claim 2 wherein the ferric ion is reduced as characterized by the reaction:

$$Ar + FeX_3 \rightarrow ArX + FeX_2,$$

wherein Ar represents an arene and X represents a halogen.

6. The process of claim 5 wherein the arene comprises xylene and the ferric salt comprises ferric chloride.

7. The process of claim 1 wherein the ferrocene comprises a compound represented by the formula:

$$(Cp)-Fe-(Cp),$$

wherein each Cp independently represents a substituted or unsubstituted eta$^5$ complexed cyclopentadienyl anion or a substituted or unsubstituted indenyl anion.

8. The process of claim 7 wherein the Cp anion ligands are independently chosen from the group consisting of an unsubstituted indenyl anion, an unsubstituted cyclopentadienyl anion, the anions of methylcyclopentadiene, ethylcyclopentadiene, n-propylcyclopentadiene, n-butylcyclopentadiene, isobutylcyclopentadiene, 1,2-dimethylcyclopentadiene, 1,3-dimethylcyclopentadiene, trifluoromethylcyclopentadiene, phenylcyclopentadiene, cyclopentadienecarboxylic acid methyl and ethyl esters, acetylcyclopentadiene, benzoylcyclopentadiene, chlorocyclopentadiene, and cyanocyclopentadiene, and mixtures thereof.

9. The process of claim 1 wherein the arene is chosen from the group consisting of benzene, toluene, o-xylene, m-xylene, p-xylene, mixed isomer xylene, mesitylene, durene, ethylbenzene, diethylbenzenes, propylbenzene, hexamethylbenzene, cumene, diisopropylbenzene, isobutylbenzene, anisole, ethoxybenzene, p-dimethoxybenzene, naphthalene, methylnaphththalenes, methoxynaphthalenes, 1,2-dihydronaphthalene, 1,2,3,4-tetrahydronaphthalene, biphenyl, diphenylmethane, triphenylmethane, diphenyl ether, stilbene, biphenylene, paracyclophane, anthracene, phenanthrene, 9,10-dihydroanthracene, fluorene, triphenylene, pyrene, perylene, chrysene, chromene, coronene, naphthacene, xanthene, thioxanthene, pyrrole, furan, benzofuran, dibenzofuran, benzopyran, carbazole, triophene, benzothiophene, indole, indene, acridine, benzoxazine, and mixtures thereof.

10. The process of claim 1 wherein the Lewis acid is chosen from the group consisting of an aluminum halide, a boron trifluoride, a gallium halide, and mixtures thereof.

11. The process of claim 1 wherein the Lewis acid is selected from a first group consisting of aluminum chloride, aluminum bromide, boron chloride, gallium chloride and a combination of a Lewis acid selected from the first group and a Lewis acid selected from a second group consisting of titanium tetrachloride, zirconium tetrachloride, hafnium tetrachloride and tin tetrachloride.

12. The process of claim 1 wherein the mixture further comprises a reducing metal selected from the group consisting of aluminum, magnesium, zinc, and mixtures thereof.

13. The process of claim 1 wherein the reaction mixture, based on one mole of ferrocene, comprises:
   from about 2 to 13 moles of arene;
   from about 0.8 to 1.2 mole ferric ion;
   from about 1.5 to 3 mole Lewis acid; and
   from about 0.1 to 1 mole of a reducing metal.

14. The process of claim 1 wherein the mixture further comprises an organic solvent that is non-reactive with the other reactants.

15. The process of claim 1 further comprising the step of quenching the reaction product by hydration of the Lewis acid.

16. The process of claim 15 wherein the quenching step comprises:
   a) adding absolute alcohol to the reaction mixture, wherein the absolute alcohol comprises methanol, ethanol or isopropanol;
   b) optionally providing external cooling; and
   c) combining the reaction mixture with a mixture of ice and water.

17. The process of claim 1 further comprising the step of exchanging the counterion of the cyclopentadienyl (II) arene complex cation with another anion.

18. The process of claim 17 wherein the ion-exchange reaction can be characterized by the reaction:

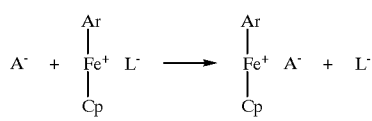

wherein:
   A is an anion of valence b where b can be 1, 2, or 3;
   Cp is an eta$^5$ complexed cyclopentadienyl anion or an eta$^5$ complexed indenyl anion,
   Ar is an eta$^6$ complexed arene anion, and
   L is a Lewis acid.

19. The process of claim 1 wherein the cyclopentadienyliron (II) cation complex reaction product comprises a complex of the formula:

$[(Cp)-Fe-(Ar)]^+{}_b A^{b-}$ wherein

Cp is an eta⁵ complexed cyclopentadienyl anion or an eta⁵ complexed indenyl anion, Ar is an eta⁶ complexed arene anion, A is an anion of valence b, and b is an integer 1, 2, or 3.

20. The process of claim 18 wherein the counterion A⁻ is chosen from the group consisting of $PF_6^-$, $SbF_6^-$, $BF_4^-$, $SbF_5OH^-$, $AsF_6^-$, $SbCl_6^-$, and $C(SO_2CF_3)_3^-$.

21. The reaction of claim 1 wherein the reaction product comprises a cyclopentadienyliron(II) arene complex chosen from the group consisting of: cyclopentadienyliron (II) m-xylene hexafluoroantimonate; cyclopentadienyliron (II) mesitylene hexafluoroantimonate; and cyclopentadienyliron (II) o-xylene hexafluoroantimonate, cyclopentadienyliron (II) p-xylene hexafluoroantimonate, and mixtures thereof.

22. The reaction characterized by the equations:

$R + Fe^{+++} \rightarrow Fe^{++} + R^+$ $2L + (Cp)_2Fe + FeX_2 + 2Ar \rightarrow 2[(Cp)-Fe-(Ar)^+(LX)^-]$ wherein the reaction of the first equation is accomplished in situ in the presence of the reaction of the second equation and wherein:

R is a reducing agent,

Cp is an eta⁵ complexed cyclopentadienyl anion or an eta⁵ complexed indenyl anion, Ar is an eta⁶ complexed arene anion, L is a Lewis acid, and X is a halogen.

23. The reaction of claim 22 characterized by the following equations;

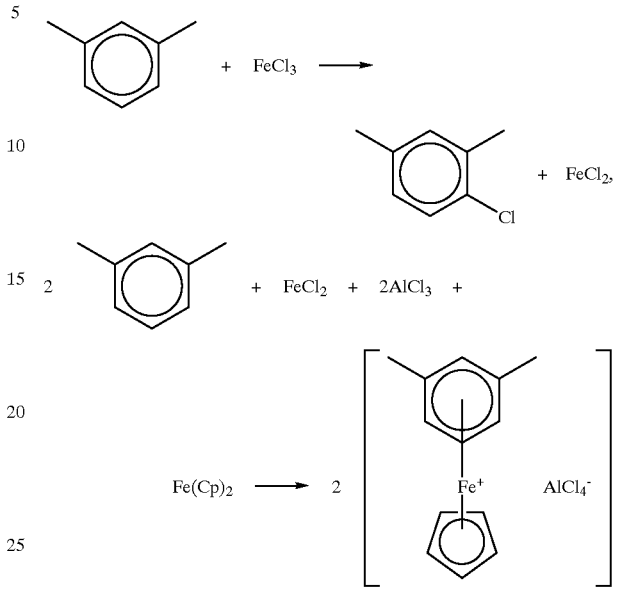

wherein Cp is an eta⁵ complexed cyclopentadienyl anion or an eta⁵ complexed indenyl anion.

* * * * *